United States Patent [19]

Cragg et al.

[11] Patent Number: 5,795,331
[45] Date of Patent: Aug. 18, 1998

[54] BALLOON CATHETER FOR OCCLUDING ANEURYSMS OF BRANCH VESSELS

[75] Inventors: Andrew H. Cragg, Edina; Jonathan Kagan, Minneapolis, both of Minn.

[73] Assignee: Micro Therapeutics, Inc.

[21] Appl. No.: 148,374

[22] Filed: Jan. 24, 1994

[51] Int. Cl.$^6$ .......................... A61M 29/00; A61M 31/00
[52] U.S. Cl. ................................. 604/96; 604/53
[58] Field of Search ....................... 604/48, 49, 53, 604/96, 101; 606/191, 192, 194, 195, 198

[56] References Cited

U.S. PATENT DOCUMENTS

| 4,207,891 | 6/1980 | Bolduc | 128/235 |
|---|---|---|---|
| 4,323,071 | 4/1982 | Simpson et al. | 128/343 |
| 4,351,342 | 9/1982 | Wiita et al. | 128/349 B |
| 4,582,181 | 4/1986 | Samson | 128/348.1 |
| 4,636,195 | 1/1987 | Wolinsky | 604/53 |
| 4,655,746 | 4/1987 | Daniels et al. | 604/53 |
| 4,661,094 | 4/1987 | Simpson | 604/53 |

(List continued on next page.)

FOREIGN PATENT DOCUMENTS

| 32 27 575 | 2/1984 | Germany | A61B 17/12 |
|---|---|---|---|
| WO 95/08289 | 3/1995 | WIPO . | |

OTHER PUBLICATIONS

Mandai et al., "Direct thrombosis of aneurysms with cellulose acetate polymer, Part I: Preliminary animal experience", *J. Neurosurg* 77:497–500, 1992.

K. Kingugasa et al., "Direct thrombosis of aneurysms with cellulose acetate polymer, Part II: Results of thrombosis in experimental aneurysms", *J. Neurosurg* 77:501–507, 1992.

W. Taki et al., "A New Liquid Material for Embolization of Arteriovenous Malformations" appearing in *AJNR* 11:163–168, jan./Feb., 1990.

T. Terada et al., "Embolization of arteriovenous malformations with peripheral aneurysms using ethylene vinyl alcohol copolymer" appearing in *J. Neurosurg* 75:655–660, 1991.

(List continued on next page.)

*Primary Examiner*—Manuel Mendez
*Attorney, Agent, or Firm*—Burns, Doane, Swecker & Mathis, LLP

[57] ABSTRACT

A method and apparatus for delivering occluding agents through an opening in a blood vessel wall and into an aneurysm chamber or a branch vessel by introducing a balloon catheter, inflating the balloon to seal the blood vessel lumen around the vessel opening, and delivering the occluding agent through the opening. The inflation of the balloon positions an exit port laterally in the vessel in alignment with the vessel opening for delivering of the occluding agent therethrough. In one embodiment, the balloon encircles the distal end segment of the catheter body, and the delivery exit port is supported on the inflated surface of the balloon. In a second embodiment, the balloon is formed and extends around a major circumferential section of the distal end segment, and the delivery exit port is formed in the remaining minor circumferential section for lateral movement into alignment with the vessel opening as the balloon fills the blood vessel on inflation. The inflated balloon maintains the occluding agent therein until it forms an occluding cast, and the balloon wall shapes the occluding cast into conformance with the blood vessel lumen. The catheter body is formed with lumens for balloon inflation/deflation, the passage over a guide wire, the delivery of the occluding agent and the venting during delivery or aspiration prior to delivery. More than one delivery exit port and associated lumen may be provided for venting during delivery and/or for the delivery of a two component occluding agent. The catheter body and the balloon are preferably formed integrally of coaxial tubes with delivery/venting lumens formed in the outer tube and a common inner lumen for inflation/deflation of the balloon, terminating in a self sealing distal valve for receiving the guide wire. Liquid occluding agents or mechanical thrombus forming devices my be delivered thereby into the aneurysm chamber or branch vessel to occlude it.

43 Claims, 7 Drawing Sheets

U.S. PATENT DOCUMENTS

| | | | |
|---|---|---|---|
| 4,693,243 | 9/1987 | Burns | 128/207.15 |
| 4,708,718 | 11/1987 | Daniels | 604/53 |
| 4,763,653 | 8/1988 | Rockey | 128/344 |
| 4,832,688 | 5/1989 | Sagae et al. | 604/53 |
| 4,994,033 | 2/1991 | Schockey et al. | 604/96 |
| 5,041,090 | 8/1991 | Scheglov et al. | 604/101 |
| 5,049,132 | 9/1991 | Shaffer et al. | 604/101 |
| 5,087,244 | 2/1992 | Wolinsky et al. | 604/53 |
| 5,090,960 | 2/1992 | Don Michael | 604/101 |
| 5,112,305 | 5/1992 | Barath et al. | 604/96 |
| 5,122,136 | 6/1992 | Gugliemi et al. | 606/32 |
| 5,188,595 | 2/1993 | Jacobi | 604/53 |
| 5,213,576 | 5/1993 | Abiuso et al. | 604/96 |
| 5,219,355 | 6/1993 | Parodi et al. | 606/191 |
| 5,222,941 | 6/1993 | Don Michael | 604/101 |
| 5,232,444 | 8/1993 | Just et al. | 604/96 |
| 5,234,437 | 8/1993 | Sepetka | 606/108 |
| 5,242,397 | 9/1993 | Barath et al. | 604/96 |
| 5,295,962 | 3/1994 | Crocker et al. | 604/101 |
| 5,318,531 | 6/1994 | Leone | 604/101 |

OTHER PUBLICATIONS

Guglielmi, G. et al., "Electrothrombosis of sacular aneurysms via endovascular approach", *J. Neurosurg.*, 75:1–7, 1991.

Higashida, R. et al., "Advances in the Treatment of Complex Cerebrovascular Disorders by Interventional Neurovascular Techniques", *Circulation*, 1991;83 [supp I]: I–196–I–206.

Purdy P. et al., "Preoperative Embolization of Cerebral Arteriovenous Malformations with Polyvinyl Alcohol Particles", *AJNR*, 11:501–510, May/Jun. 1990.

Rosenthal, D. et al., "Endovascular infrainguinal in situ saphenous vein bypass: A multicenter preliminary report". *J. Vasc. Surg.*, 1992: 16:453–8.

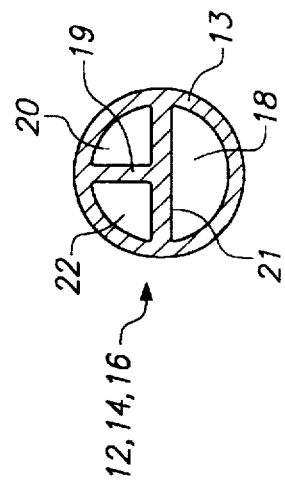
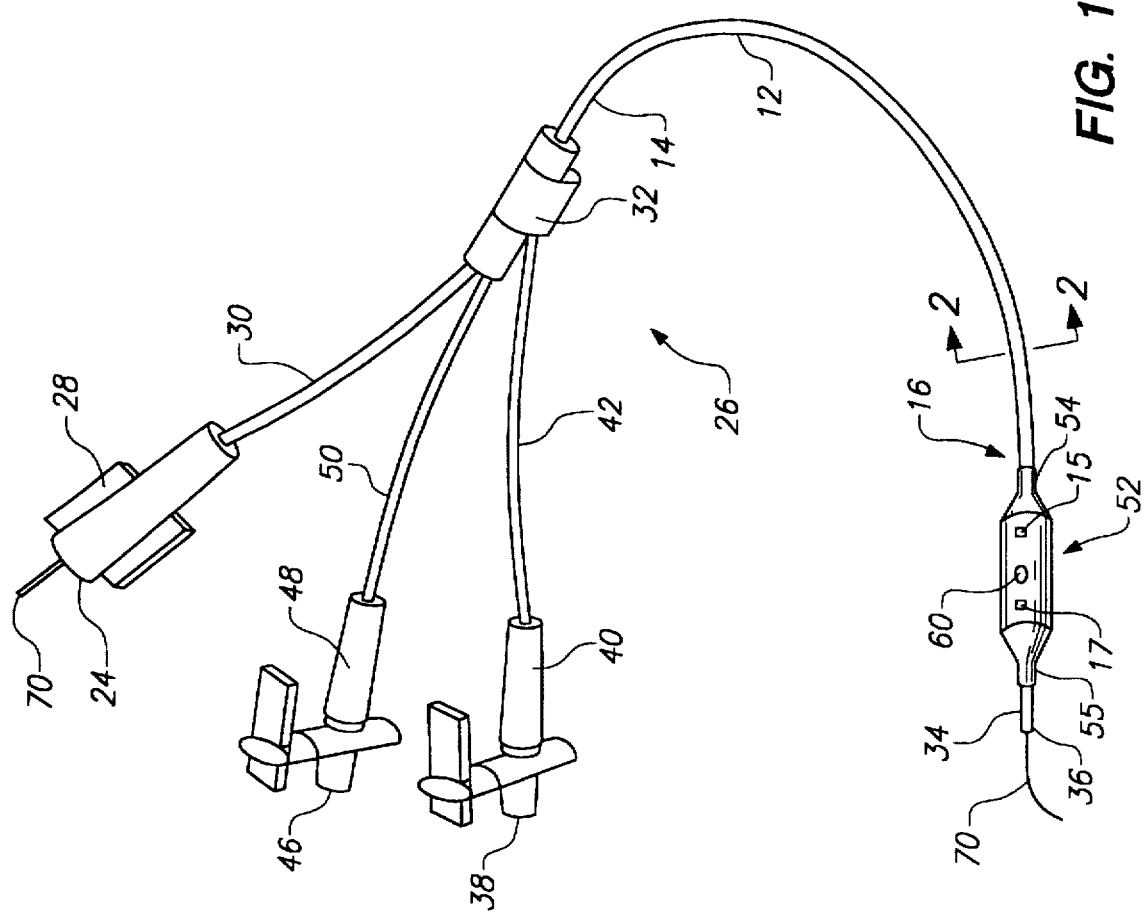
FIG. 2
FIG. 1

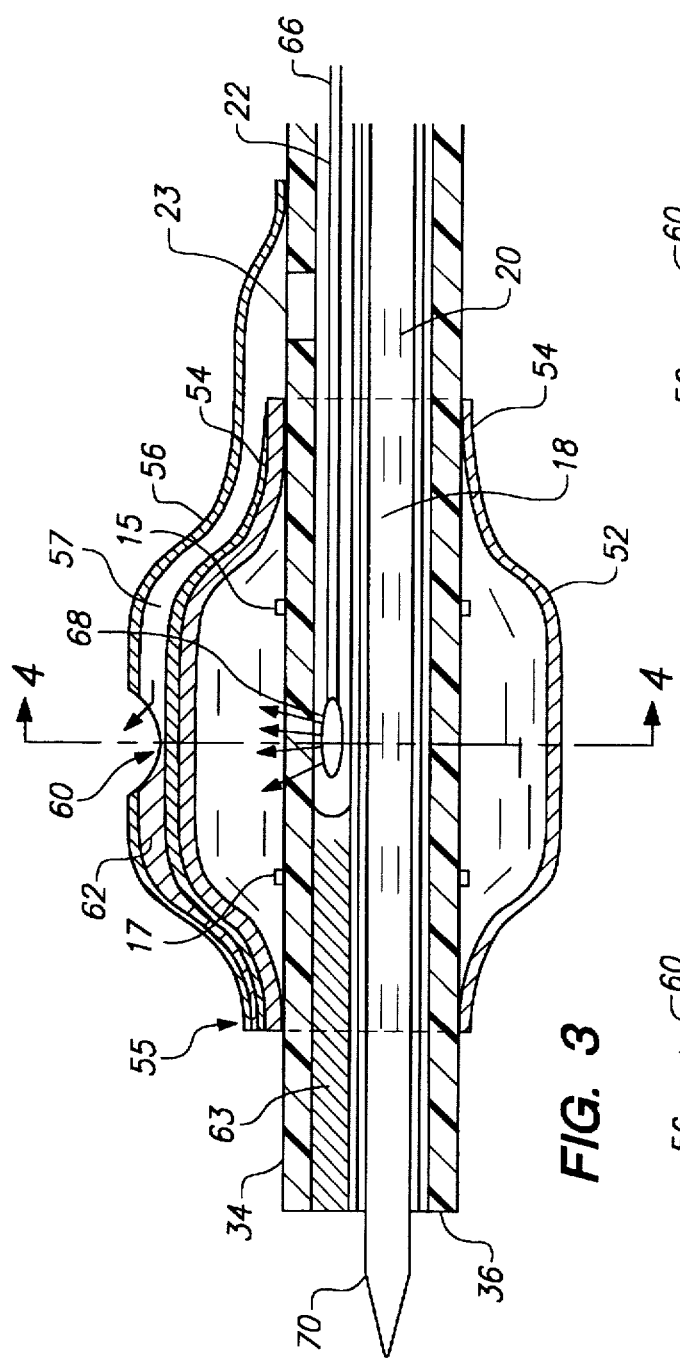
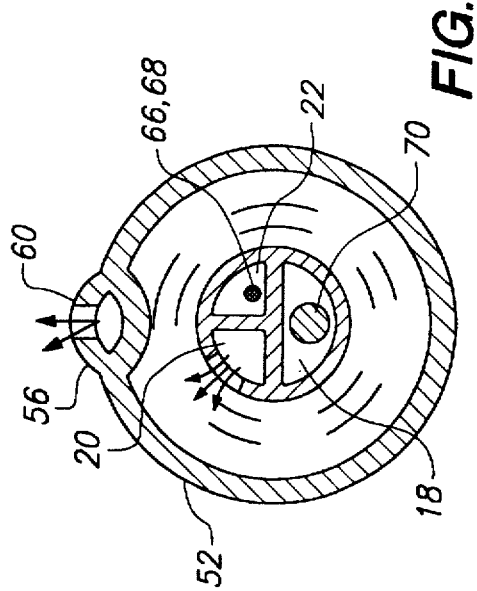
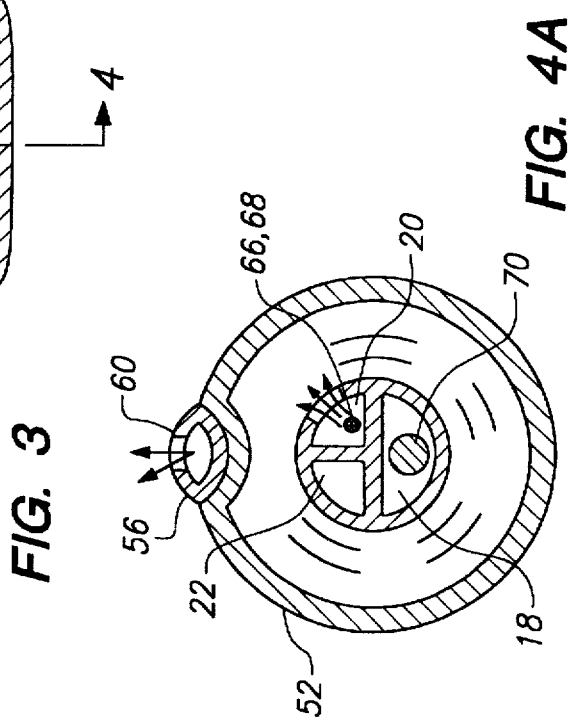
FIG. 3
FIG. 4A
FIG. 4B

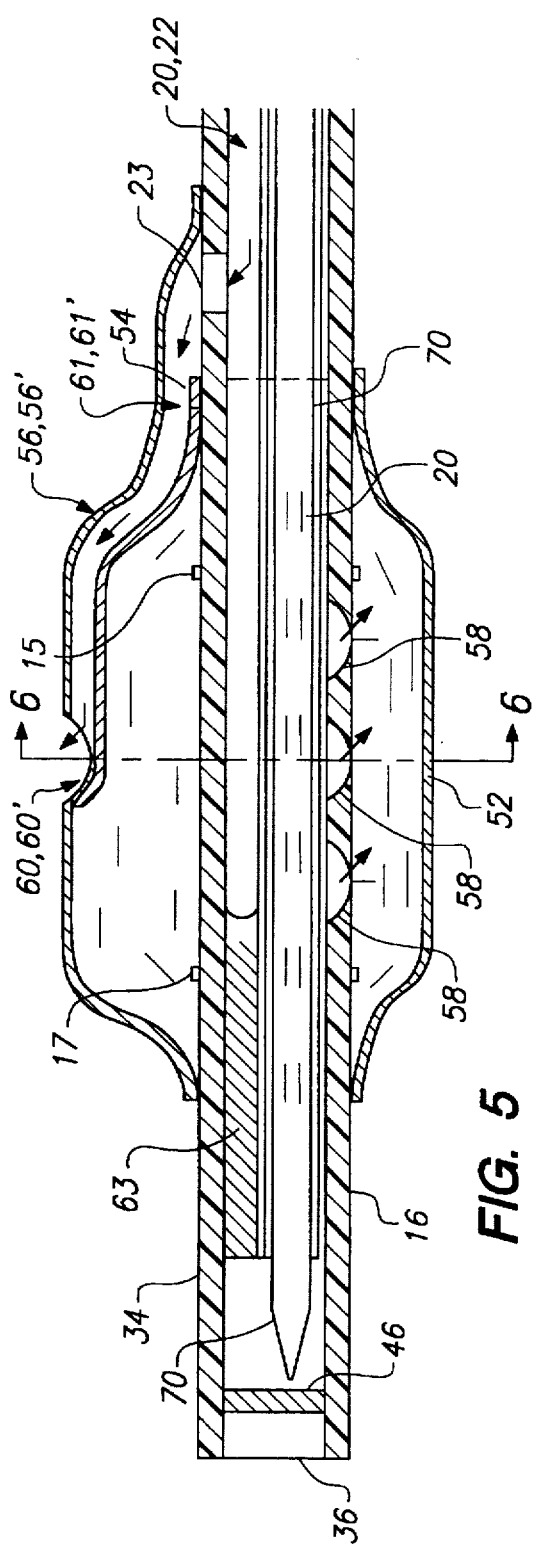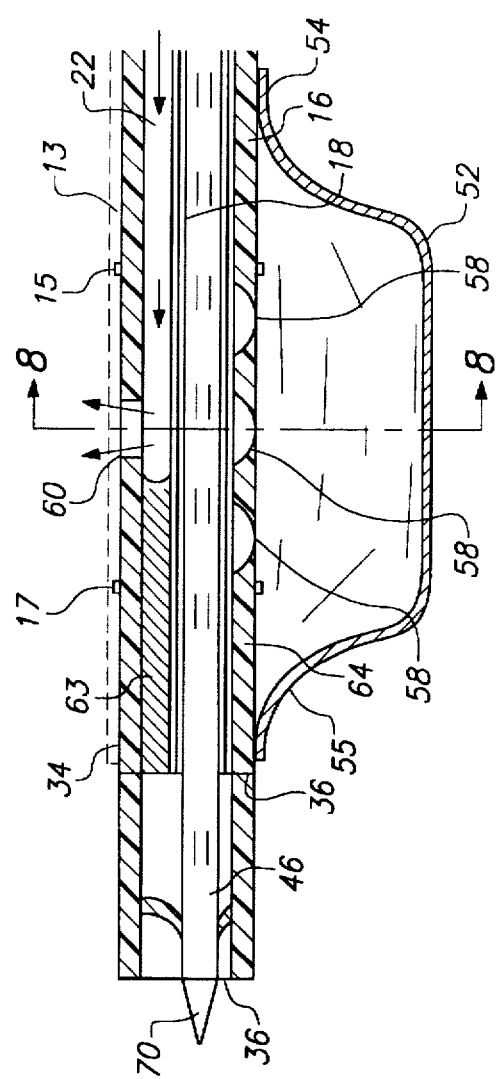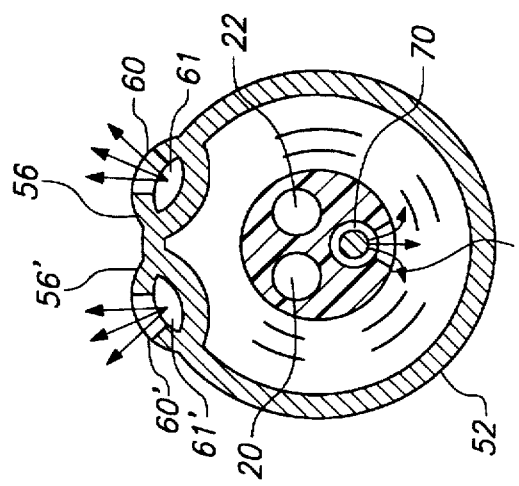

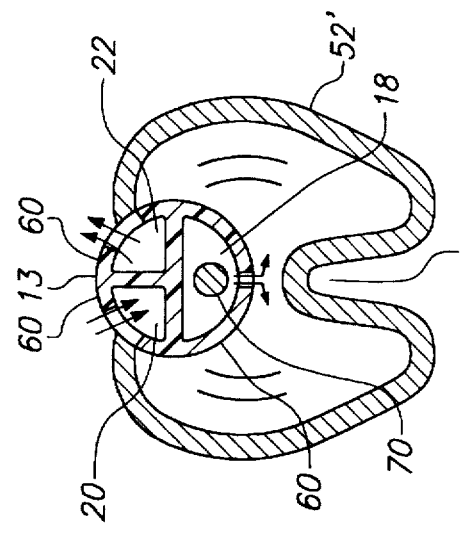
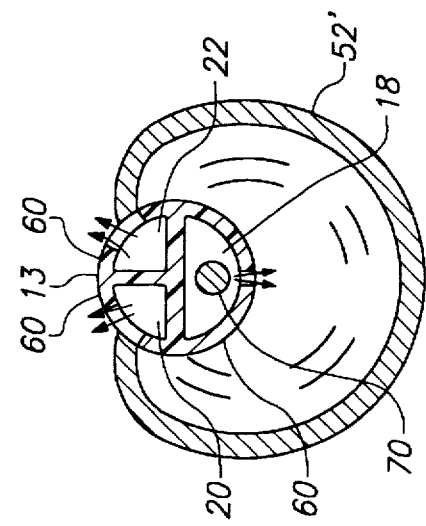
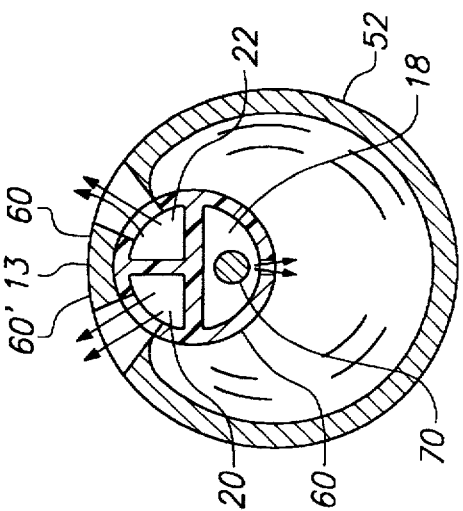
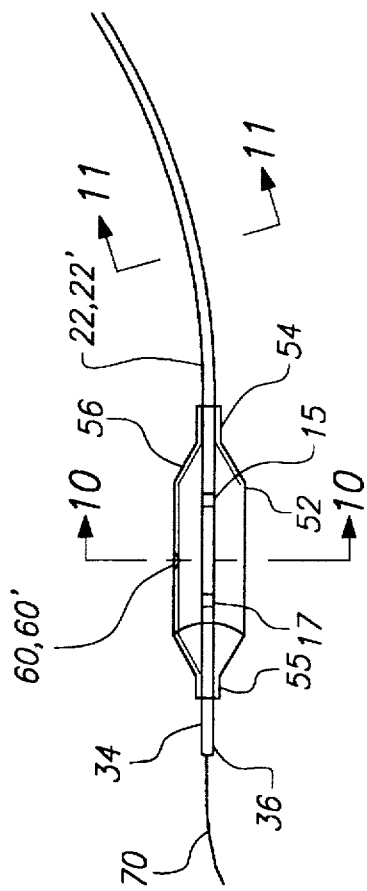
FIG. 8A
FIG. 8B
FIG. 8C
FIG. 9

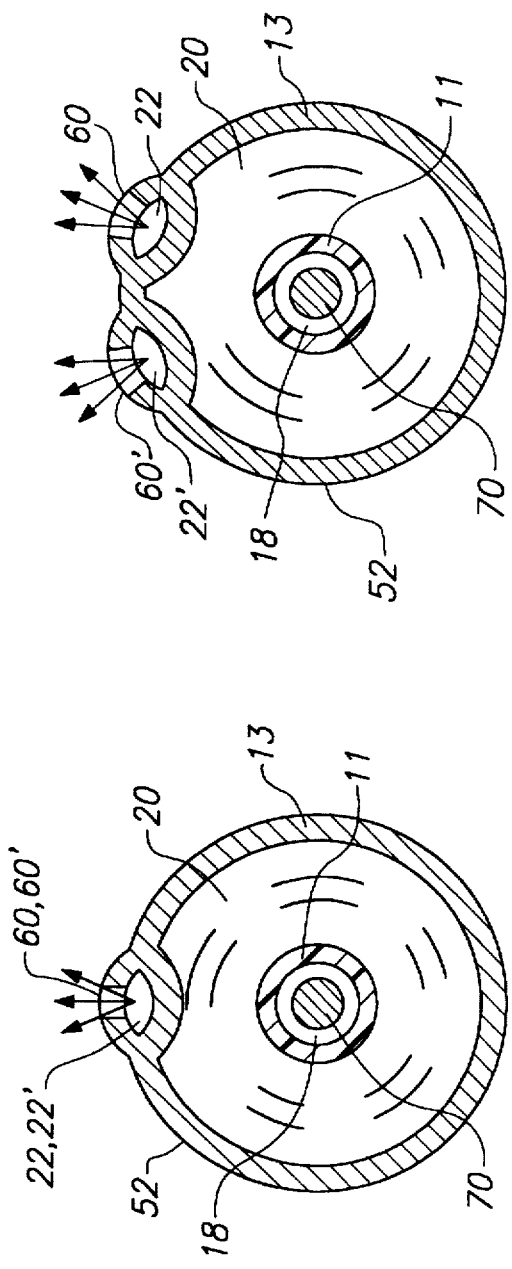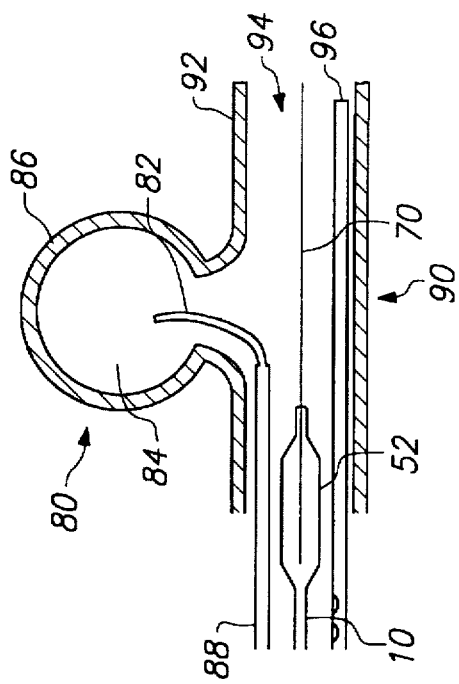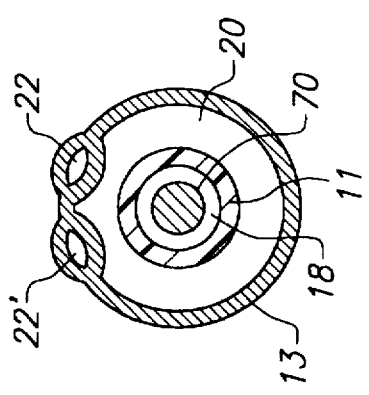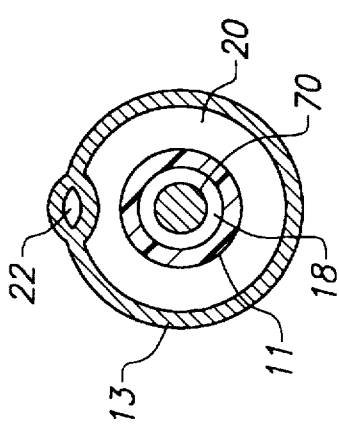

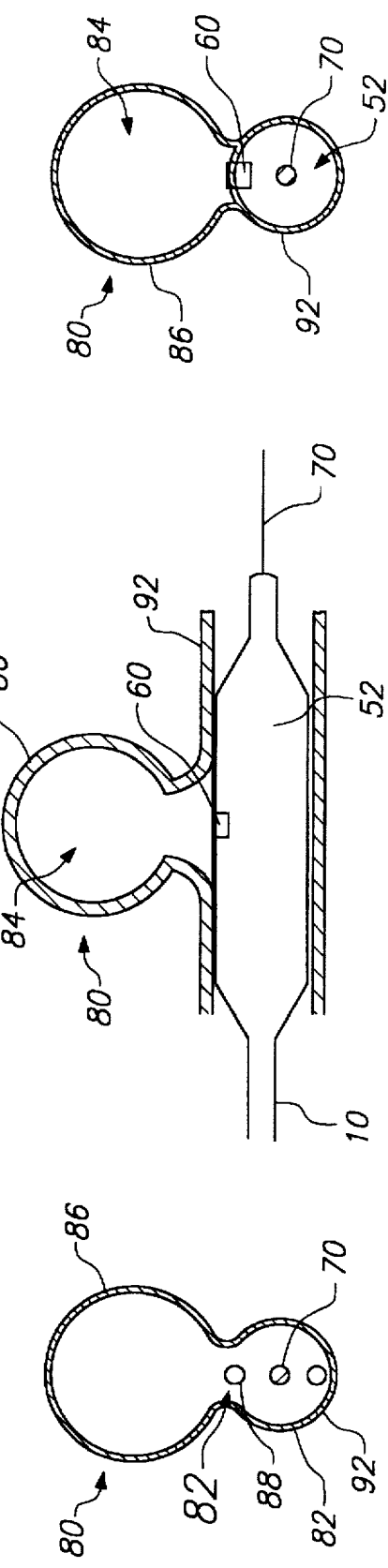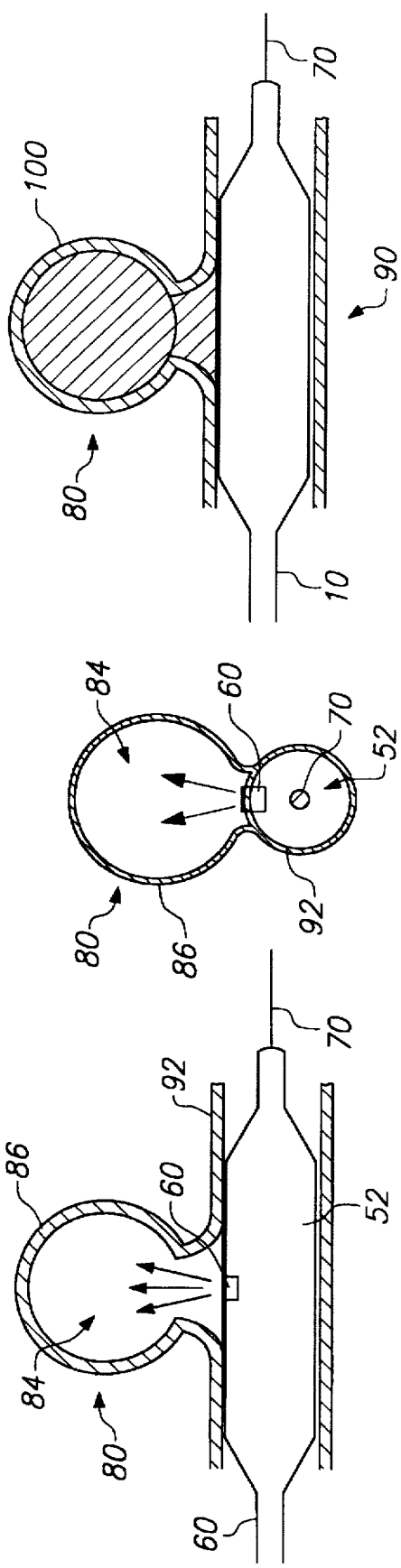

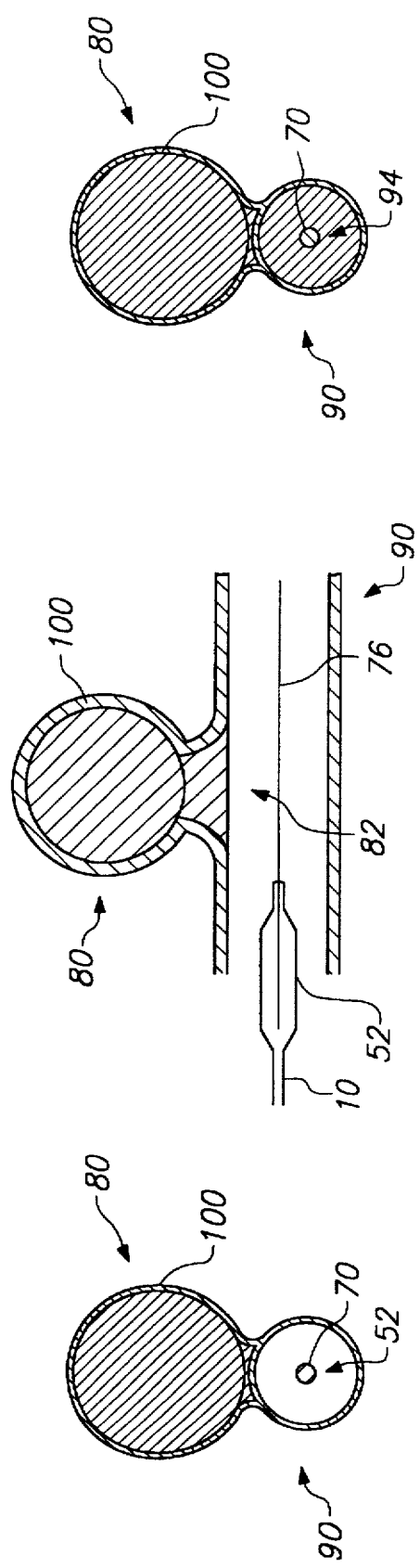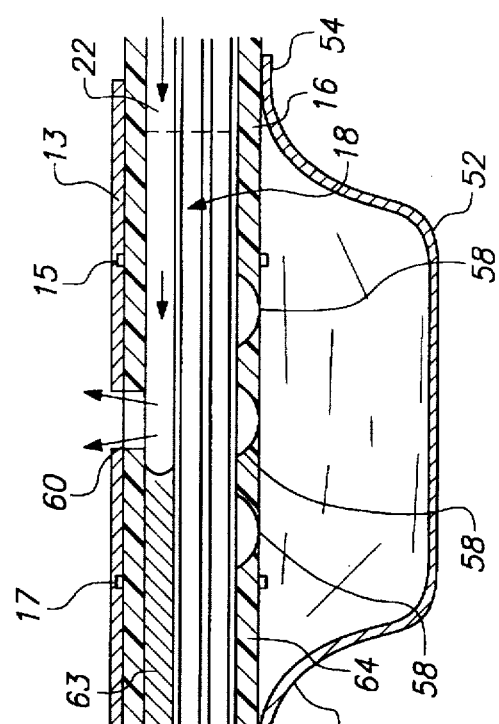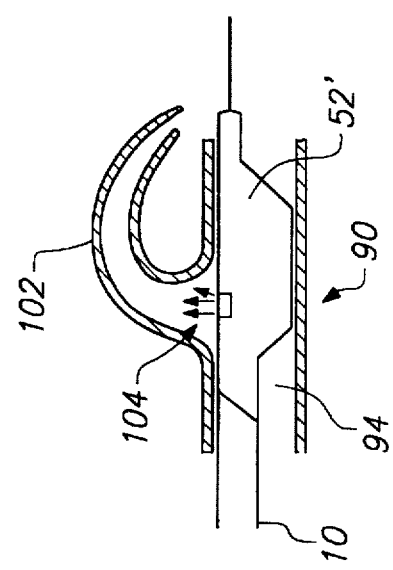

BALLOON CATHETER FOR OCCLUDING ANEURYSMS OF BRANCH VESSELS

BACKGROUND OF THE INVENTION

1. Field of the Invention

The present invention relates to a method and apparatus for delivering occluding agents through the opening in a blood vessel wall and into the aneurysm chamber or into a peripheral vessel, and in particular by introducing a balloon catheter, inflating the balloon to seal the blood vessel lumen around the vessel opening, and delivering the occluding agent through the opening to prevent loss of occluding agent into the blood vessel during such delivery and until in situ stabilization of the occluding agent as an occluding cast shaped to retain the patency of the blood vessel at the occluded opening.

2. Description of the Background Art

The occurrence of aneurysms in weakened blood vessel walls, particularly in arterial blood vessels, often presents a life threatening risk to a patient. This is particularly true in blood vessels serving the heart, brain and other vital organs. In both venous and arterial blood vessels, such aneurysms may rupture, causing internal bleeding and loss of blood pressure or become the source of clots that may become dislodged and are borne by moving blood to other sites where they restrict blood flow. In major arteries, the rupture may lead to severe loss of pressure and rapid death. In the brain, the pooling of blood may lead to pressure on brain cells and result in a stroke.

The invasive, surgical removal of aneurysms and closure of the opening in the vessel wall itself presents a grave risk to the patient and poses severe post-operative complications. Conventional vascular surgery or micro-surgery may be employed successfully to correct aneurysms of vessels accessible to such surgical approach. However, the most threatening aneurysms are often deep within a vital organ or large in size and having a wide neck where the trauma of surgical treatment presents a great risk.

One surgical treatment for dealing with such aneurysms involves closing off the blood vessel and thereby sacrificing it and tissue that it serves to ischemia. This type of occlusion may be employed as a last resort in cases where the induced trauma presents the lesser evil.

It is therefore often either impossible to proceed surgically or preferable to avoid such surgical procedures. Less invasive approaches have been proposed and tested either in animals or clinically for closing off the aneurysm opening and/or filling the aneurysm sac. For example, as described in U.S. Pat. No. 5,041,090, a number of approaches have been undertaken employing catheters for positioning detachable balloons either in the aneurysm sac or in the adjacent vessel, filling the balloon with a quick setting polymer and detaching the balloon in attempts to either fill and displace blood in the aneurysm sac or effect stationary occlusion of the vessel. In the '090 patent, a pair of catheter borne, detachable balloons are provided that are intended to be placed in the aneurysm sac, inflatable with one balloon inside the other, and inflated to fill with one material or polymerize another material in the outer balloon in a shape conforming to the aneurysm sac, so that the catheters may be detached with the balloons remaining in place. In one embodiment, polymerizable material appears to be directed out of multiple holes in the outer balloon and into contact with the wall of the aneurysm to bond the balloons and wall together.

In all of these procedures, it is necessary to get a balloon or balloons directed through the neck of the aneurysm and retained there. The inflated balloon or balloons may protrude out through the opening of the aneurysm and interfere with blood flow through the vessel lumen. Material emitted from holes in a balloon in the aneurysm chamber may be forced out the opening and block the vessel lumen. Moreover, the introduction of the balloon catheter or catheters into the aneurysm chamber itself poses the risk that the aneurysm wall will be punctured.

Further approaches to encouraging thrombus formation in aneurysm chambers are described in U.S. Pat. No. 5,234,437 wherein a plurality of metallic vaso-occlusion coils are placed in the chamber by positioning a pusher catheter into the opening and detaching the coils. Detachment is proposed by applying current of electrically sever the connection or by threading the coil out of engagement with the pusher mechanism. See also, for example, "Electro Thrombosis of Aneurysms" *J. Neurosurgery*, 75:1–7, January, 1991 by Guglielmo, where electric current is employed as well. These approaches require the proper introduction of a catheter into the opening, and the positioning of such catheters is difficult and presents the risk of perforating the aneurysm wall.

In a still further approach described in U.S. Pat. No. 5,219,355, a catheter borne sleeve is proposed to be placed across and within the depicted wide mouth opening of an aneurysm to block the mouth and serve as an alternative, intraluminal blood vessel. The sleeve is attached at either end to a pair of expandable stents which are introduced by a double balloon catheter and expanded upon inflation of the balloons. Presumably, the expanded stents stabilize the sleeve ends against patent blood vessel walls. In this approach, an apparent risk lies in detachment of one or both of the stents from contact with the blood vessel walls over time. Alternatively, as the stents fibrose in, the fibrosis may restrict blood flow and lead to further complications. Many blood vessels would appear to be too small to benefit from this approach due to the necessary size of the components and introducing apparatus.

Spaced apart, double balloon catheters are also proposed for use in temporarily occluding blood vessels to introduce a therapeutic agent in treating blood vessel intima injured in balloon angioplasty procedures, as disclosed in U.S. Pat. No. 4,832,688.

Further spaced apart balloon catheters have been proposed for isolating a network of small branch blood vessels collaterally supplying a tumor and injecting a contrast material or a small vessel occlusive collagen material into the network, as disclosed in U.S. Pat. Nos. 4,655,746 and 4,708,718. The injected material is delivered directly into the vessel between the two inflated balloons and described as being drawn into the small diameter branch blood vessels and remaining there over a period of time to occlude them. The disposal of the collagen material remaining in the main vessel is apparently not explained. To the extent that the solidified collagen remains in the secondary and tertiary vessels after withdrawal of the catheter, it may protrude out of these minor branch vessels into the lumen of the main vessel and provide sites for the development of thrombi or stenosis.

In addition, single or co-axially disposed double balloon catheters of the type disclosed in U.S. Pat. Nos. 5,049,132, 5,087,244, 5,112,305, and 5,213,576 are described for distributing therapeutic agents through side wall holes in the outermost balloon to vessel walls to treat an atherosclerotic plaque or to induce penetration of the agent into the vessel wall to treat a vessel wall tumor or for applying heparin post-operatively at the site of an angioplasty procedure. These balloon catheters infuse therapeutic agents into the vessel itself and are not suited to the introduction of an occluding agent of a type that would also occlude an aneurysm chamber or branch vessel.

In a further surgical procedure for harvesting saphenous veins for use in bypass surgery, it is known to strip out the saphenous vein section, remove the vein valves and tie off the branching vessels to prepare the section for implant as a bypass artery section. It is also known to do an in situ bypass converting a section of a vein adjacent a blocked artery section into a substitute artery section. The vein section is tied off proximally and distally, severed, and the two ends are grafted to the artery. In order to prepare the vein section, it is necessary to excise any venous valves in the vein section lumen and to tie off any peripheral or side branch veins. See, for example, "Endo-Vascular Infrainquinal In Situ Saphenous Bypass: A Multi Center Report", *J. Vascular Surgery*, 1992;16:453–458, by Rosenthal.

To avoid the surgery to expose the length of the sacrificed vein section to tie off the side branches, it has been proposed steer a catheter into the side branches and deposit occlusion coils therein to occlude the vessels. It would be desirable to effect a more efficient way of closing off the side branch vessels without invasive surgery.

Despite the advances and improvements in treatments for various conditions that have been introduced in recent years through the use of balloon catheters, a need remains for an apparatus and method for intraluminally occluding aneurysms in a main blood vessel wall that is simple to practice, does not threaten the integrity of the adjacent main blood vessel, and wherein main vessel patency is rapidly restored.

Where absolutely necessary, a need exists for such an apparatus and method which may be used to seal off and occlude a peripheral vessel feeding an aneurysm or for other reasons, e.g. the preparation of a vein for use as an arterial bypass section.

SUMMARY OF THE INVENTION

It is therefore a principal object of the present invention to provide an apparatus and method which provides for the isolation and sealing off of an opening in a blood vessel of an aneurysm chamber or a branching, minor blood vessel in situ without occluding the main blood vessel.

It is a further principal object of the present invention to seal an opening to an aneurysm chamber in situ to allow evacuation of the chamber and direction of an occluding agent through the opening to maintain it in the aneurysm chamber until occlusion is completed without compromising blood flow through the vessel.

It is a still further principal object of the present invention to seal off a blood vessel aneurysm chamber in situ from its blood vessel for the treatment of the aneurysm without the necessity of introducing a catheter or balloon directly into the aneurysm chamber and without sacrificing the vessel by occluding it.

It is yet a further object of the present invention to provide an apparatus and method for sealing off a minor or peripheral blood vessel at its opening to a main blood vessel in situ which allows evacuation of the peripheral vessel and direction of an occluding agent through the opening of the peripheral vessel and to maintain the occluding agent therein until occlusion is completed without compromising blood flow through the vessel.

In accordance with these and other objects, a method and apparatus is provided for forming an occluding cast through a vessel opening in the side wall of a main blood vessel for occluding a peripheral vessel or aneurysm outside of the opening without occluding the vessel, comprising the steps of and means for sealing the main vessel from the vessel opening into the aneurysm or peripheral vessel, delivering an occluding agent through the vessel opening into the aneurysm chamber or peripheral vessel, and maintaining the seal until occlusion is effected or the agent is stabilized and the occluding cast is formed.

If necessary to effect occlusion, the apparatus and method further comprises means for and the method step of aspirating the contents of the aneurysm chamber or peripheral vessel through the opening thereof before introducing the occluding agent and/or venting the contents of the aneurysm chamber or peripheral vessel through the opening thereof during introducing the occluding agent.

Preferably the sealing and delivery means for and steps of further comprise introducing a balloon catheter having an inflatable balloon and a delivery lumen extending therethrough terminating in a delivery exit port into a position in the main vessel adjacent to the opening, orienting the delivery exit port to the opening, and inflating the balloon to fill the blood vessel and to seal the delivery exit port and the opening from the blood vessel lumen. The delivery means and step is accomplished by delivering the occluding agent through the delivery lumen and delivery exit port, and through the opening to form a cast that does not occlude the vessel.

Preferably, the balloon catheter has a plurality of lumens extending to a distal segment thereof to inflate/deflate the vessel filling balloon in the distal segment, to aspirate or vent the aneurysm or peripheral vessel through an aspiration/vent port, to deliver the occluding agent through a delivery exit port or ports formed adjacent the balloon thereof, and to accept a guide wire for positioning the distal segment in the location of treatment. Alternatively, the aspiration and/or venting may be accomplished employing a separate catheter.

The method of use of the balloon catheter comprises introducing and advancing the balloon catheter through a patient's blood vessels until the distal segment bearing balloon is positioned alongside the opening of an aneurysm or peripheral vessel, orienting the exit port of the delivery lumen toward the opening, inflating the balloon to fill the vessel lumen and isolate it from the opening, aspirating blood from the opening, if necessary, introducing an occluding agent through the delivery lumen out the delivery exit port and through the opening and filling the aneurysm chamber or peripheral vessel with the occluding agent, maintaining the inflated balloon in place for a time period sufficient to stabilize the occluding agent and form the occluding cast, and deflating and withdrawing the balloon catheter. If necessary, the venting may take place during the filling step. Optionally, the balloon may be rotated after delivery of the occluding agent to present a solid balloon wall across the vessel opening for shaping the occluding cast at the opening into conformance with adjacent blood vessel lumen walls.

The orientation of the delivery exit port to the opening is preferably determined through the use of radiopaque markers around the ports which may be observed through fluoroscopy. The proper seal afforded by the inflated balloon may be verified in a further step of inflating the balloon and injecting a contrast medium through the delivery lumen and exit port after orienting the delivery exit port to a trial position and observing the filling of the aneurysm as well an the absence of its leakage down the vessel lumen when it is properly oriented. Alternatively, a radiopaque tip probe may be introduced down the delivery lumen and observed as it exits the exit port and enters the aneurysm chamber or a pressure measurement may be taken.

The "occluding agent" preferably comprises liquid or solid materials or objects that effect occlusion through a variety of reactions. The occluding agent is preferably introduced as a liquid and hardens within the aneurysm chamber. In a first variation, the occluding agent may require a reactive catalyst to harden, and the balloon catheter may be provided with a further lumen and exit port adjacent to the first exit port and a further delivery lumen for separately introducing the catalyst. In a further variation, the occluding agent may react to radiation of a certain wavelength which is provided from an external source and introduced into the distal segment of the balloon catheter and directed at the opening to effect hardening of the delivered occluding agent by a light conductor or optical fiber.

Alternatively, the occluding agent may comprise a blood coagulating material or mechanism, e.g. one or nore expandable coils, may be compressed and introduced transluminally and positioned through the exit port and through the opening, where the mechanism expands into contact with the aneurysm walls to induce coagulation of blood in the chamber or the peripheral vessel.

In a preferred embodiment, the balloon catheter any be provided with a guide wire lumen and guide wire exit port distal to the balloon or use with guide wire for easing introduction and advancement of the balloon catheter. The balloon inflation/deflation lumen may be provided with a distal guide wire receiving valve for allowing advancement of the guide wire distally or introduction of the balloon catheter over the previously introduced and positioned guide wire while allowing inflation of the balloon through the same inflation/deflation lumen.

The catheter body may alternatively be formed with a permanently installed guide wire or other means extending its length to transmit rotational torque from the proximal to the distal end segment to rotate the distal end segment for positioning of the exit port(s) of the respective delivery and/or venting lumen(s) in alignment with the vessel opening. The rotation may also be employed to rotate the inflated balloon to seal off the vessel opening from the exit port(s) after delivery of the occluding agent until the occluding cast is formed.

In order to optimally position the exit port or ports of the delivery lumen or lumens, at least a distal section of the delivery lumen(s) may be disposed against the outer wall of the balloon in a first embodiment. The inflation of the balloon disposes the delivery exit port(s) to one side of the expanded balloon, and the expanded balloon presses generally radially outwardly of the catheter body. The distal section of the delivery lumen(s) expends with the expanding balloon well.

In a second embodiment of the balloon and delivery lumen structure, the delivery lumen(s) is disposed within the catheter body through its length and terminates in the delivery exit port(s) in one side quarter section of the catheter body. The balloon may be formed in the remaining three quarter section of the exterior surface of the catheter body. The expanding balloon presses the catheter body radially away so that the exit port(s) is pressed into the aneurysm opening.

In either balloon embodiment a further separate catheter may be introduced alongside the inflated portion of the balloon, and enveloped thereby along a portion of its length, to provide a lumen allowing blood flow in the vessel to bypass the balloon. Alternatively, the balloon may be shaped to form a blood flew passageway with the blood vessel wall opposite to the wall that the exit port(s) are disposed toward. In either case, the bypass allows the balloon catheter to be placed for a longer period of time for slower setting occluding agents.

Advantageously, the balloon catheter for treating aneurysms of the present invention allows the isolation of the opening of the aneurysm chamber or the peripheral vessel from the main vessel lumen and the introduction of occluding agents only into the opening where they can act or set up to only fill or close the aneurysm chamber or peripheral vessel. The balloon catheter may be used in other applications, e.g. for sealing branch peripheral veins of a vein harvested for use in bypass surgery.

The balloon catheter for is particularly advantageous for use in difficult to access vessels and for occluding aneurysms having wide neck openings along one side of a blood vessel. The introduction process is simple and does not involve complex maneuvers to steer or turn the distal segment which is important in small vessels and reduces operative time.

The reduced leakage of occluding agent back into the main vessel decreases the risk of vessel blockage and/or stenosis and resultant tissue ischemia. Patient comfort is increased and cost of the intensive care treatment is reduced by the shortened time and reduction of exposure to the occluding agent.

BRIEF DESCRIPTION OF THE DRAWINGS

These and other objects, advantages and features of the invention will become apparent from the following detailed description of the preferred embodiments of the invention, and in which:

FIG. 1 is a perspective view of one embodiment of the balloon catheter for occluding aneurysms or blood vessels of the invention;

FIG. 2 is an end cross section view of one embodiment of the catheter body lumens of the catheter of FIG. 1;

FIG. 3 to a partial side cross section view of a first embodiment of the balloon structure and delivery exit port of the distal end segment of the catheter of FIG. 1;

FIG. 4A is an end cross section view of the first embodiment of the balloon structure and delivery exit port of the catheter of FIG. 3;

FIG. 4B is an end cross section view of a variation on the first embodiment of the balloon structure and delivery exit port of the catheter of FIG. 3;

FIG. 5 is a partial, side cross section view of a further embodiment of the balloon structure and delivery exit port of the catheter of FIG. 1 for delivering a two component occluding agent through separate delivery lumens or for venting while delivering a single component occluding agent, and including a view of a distal valve for allowing the guide wire lumen to also function as an inflation/deflation lumen;

FIG. 6 is an end cross section view of the further embodiment of the balloon structure and delivery exit ports of the catheter of FIG. 5;

FIG. 7 is a partial, side cross section view of a second embodiment of the balloon structure and delivery exit ports of the catheter of FIGS. 3 or 5;

FIG. 8A is an end cross section view of the second embodiment of the balloon structure of the catheter of FIG.

7 configured to deliver a two component occluding agent through adjacent exit ports;

FIG. 8B is an end cross section view of the second embodiment of the balloon structure of the catheter of FIG. 7 depicting a further inflated balloon cross-section shape for accommodating blood flow past the balloon on inflation in a blood vessel and configured to deliver a single component occluding agent while venting through adjacent exit ports;

FIG. 8C is a further end cross section view of the second embodiment of the balloon structure of the catheter of FIG. 7 depicting a further method of forming the balloon structure;

FIG. 9 is a perspective view of a further embodiment of the balloon catheter for occluding aneurysms or blood vessels of the invention fabricated with an integral balloon and lumen(s) formed in the balloon wall and outer catheter body tube;

FIG 10A is an end cross section view of the further embodiment of FIG. 9 depicting the balloon structure supporting a single lumen and delivery exit port;

FIG. 10B is an end cross section view of the further embodiment of FIG. 9 depicting the balloon structure supporting a double lumen and delivery exit ports;

FIG. 11A is an end cross section view of the catheter body of the embodiment of FIG. 9 having a single delivery lumen formed in the outer tube;

FIG. 11B is an end cross section view of the catheter body of the embodiment of FIG. 9 having two delivery lumens formed in the outer tube;

FIG. 12A is a schematic side view illustration of an aneurysm in an artery and the positioning of a deflated balloon catheter in relation to the aneurysm opening in accordance with the invention, as well as the optional positioning of separate venting and bypass catheters;

FIG. 12B is an end view of the illustration of FIG. 12A;

FIG. 13A is a schematic side view illustration of the aneurysm and the inflation of the balloon of the balloon catheter, in accordance with the embodiments of the invention in which the exit port or ports are borne on the balloon, to effect a seal of the aneurysm opening;

FIG. 13B is an end view of the illustration of FIG. 13A;

FIG. 14A is a schematic side view illustration of the aneurysm and delivery if occluding agent through the opening in accordance with the embodiments of the invention;

FIG. 14B is an end view of the illustration of FIG. 14A;

FIG. 15A is a schematic side view illustration of the opening and the aneurysm filled with occluding agent and maintained there by the inflated balloon until it forms a solid occluding cast;

FIG. 15B is an end view of the illustration of FIG. 15A;

FIG. 16A is a schematic side view illustration of the deflation of the balloon and withdrawal of the balloon catheter leaving the occluding cast in position in accordance with the embodiments of the invention;

FIG. 16B is an end view of the illustration of FIG. 16A;

FIG. 17 is an alternative schematic side view illustration of FIG. 15A wherein the balloon catheter is introduced with the deflated balloon in relation to the opening of a branch vessel to a main blood vessel to effect the occlusion thereof in the manner of FIG. 12–16; and FIG. 18 depicts an alternate distal end segment of the balloon catheter of the various embodiments having a permanently installed torque wire attached therein for allowing rotation of the balloon.

The drawing figures are not necessarily to scale.

DETAILED DESCRIPTION OF THE PREFERRED EMBODIMENTS OF THE INVENTION

In the following description, the several alternative preferred embodiments share common features of the invention which are illustrated generally in FIG. 1 and more specifically in other figures. The methods of using the various embodiments to deliver an occluding agent and form an occluding cast in an aneurysm chamber or a branch vessel are illustrated schematically in FIGS. 12–17. The term "occluding agent" as defined above is intended to encompass the various liquid and solid materials and devices described herein which solidify or set up in situ or which encourage the formation of thrombus which occlude the aneurysm chamber or branch vessel.

The balloon catheter 10 of the present invention includes a length of multi-lumen flexible tubing forming a catheter body 12 having a proximal end segment 14 and a distal end segment 16. The catheter body 12 is preferably formed with a plurality of axially extending, co-linear passageways or lumens, e.g. the three lumens 18, 20 and 22 depicted in the cross section view of FIG. 2 (and in further views) which are coupled to structure in the proximal and distal segments to function as a balloon inflation/deflation lumen and/or a guide wire lumen and as one or two delivery lumens. In other words, the three lumens 18, 20 and 22 can be configured to deliver a single form of occluding agent in one embodiment of the invention or to deliver two separate components of an occluding agent, e.g. a catalyst and an active ingredient, in a further embodiment of the invention as described in greater detail hereafter. Alternatively, one lumen may be used to vent or aspirate through the opening to assist in filling the aneurysm chamber or branch vessel with the single occluding agent. Four lumens may also be provided to deliver the two components or perform other functions.

In any such configuration, the tubing of the catheter body 12 may be extruded from flexible plastic materials, e.g. thermoplastics, polyvinyl chlorides, polyethylenes, polyurethanes, polyesters, polypropylenes or the like as is well known in the balloon catheter art. The catheter body may be extruded or formed with a variety of lumen cross sections, including circular or elliptic lumens (as shown in FIG. 6) or in a co-axial configuration (as described with reference to FIGS. 9–11) or with the pie-shaped lumens depicted in FIG. 2.

As shown in FIG. 2A, the lumens 18, 20 and 22 are separated by webs 19 and 21 and confined in an outer tube 13. Lumen 18 is larger in cross section in order to accommodate a guide wire 70 shown in cross section. Lumens 20 and 22 are oriented together on one side to facilitate their alternate employment as delivery or venting lumens in the various embodiments described below.

Returning to FIG. 1, the lumens 18, 20 and 22 are coupled through a manifold 32 at the catheter body proximal end segment 14 to a catheter proximal end connector assembly 26. One of the lumens, e.g. lumen 18, is coupled through manifold 32 to a single lumen tube 30 and proximally terminates in a fitting 28 into the aperture 24 of which a guide wire 70 may be inserted. In one embodiment, the guide wire lumen 18 is not employed for any other function, although it may also be employed as the balloon inflation/deflation lumen in other embodiments.

The second lumen 20 is coupled through manifold 32 to a tube 42 which is coupled in turn to a valve adaptor 40. The second lumen 20 may be coupled internally to the balloon 52 to function in one embodiment as an inflation/deflation lumen when it is fitted to a source of pressurized fluid (not shown) attached at adaptor fitting 38. In another embodiment, the lumen 20 may be in communication with a further delivery exit or venting port 60' adjacent to delivery exit port 60 and employed to deliver a component of a two component occluding agent or as an aspiration and/or venting lumen.

The third lumen 22 is coupled through manifold 32 to a tube 50 which is coupled in turn to a valve adaptor 48. The third lumen 22 may be coupled internally at the proximal junction 54 of the balloon 52 with the lead body 12 through an elastic tube extension formed either inside or outside the balloon in various embodiments and extending along the outer wall of the balloon 52 to a delivery exit port 60 positioned midway down the length of the balloon 52. The third lumen 22 functions in all of the embodiments as a conduit for the delivery of a contrast medium or occluding agent, as described hereafter, upon positioning of the delivery exit port with respect to the opening of an aneurysm and inflation of the balloon 52. The third lumen may also be employed to introduce further catheters or devices into proximity with the opening 60 as described below.

The balloon catheter 10 terminates at its distal end junction 55 with a soft tip 34 and a tip aperture 36 through which the guide wire 70 may extend during introduction of the catheter 10 and positioning of the balloon 52 alongside the aneurysm. The distal end segment 16 of the catheter body 12 is also provided with first and second radiopaque markers 15 and 17 which are located with respect to the delivery exit port 60 to assist in aligning it to the opening of an aneurysm or a branch vessel during introduction and orientation of the distal end segment 16. Any of the well known techniques may be employed for arterial and venous introduction of the catheter 10, with or without use of a surrounding introduction catheter (not shown) or the guide wire 70.

Turning now to FIGS. 3 and 4A, they depict in a partial side cross section view and end view, one embodiment of the construction of the balloon 52 in relation to the catheter body 12, its lumens 18, 20, 22, and the tube extension 56 leading to the delivery exit port 60. In this cross section view, the lumens 20 and 22 are filled proximal to the distal aperture 36 to isolate the lumens and allow their use to deliver occluding agent and inflation fluid respectively. The inflation/deflation lumen 20 terminates and is filled more distally within the distal junction 55 of the balloon 52 with the outer surface of the lead body 12. The portion of the inflation/deflation lumen 20 within the balloon 52 has a number of spaced inflation/deflation holes 58 through the outer wall of the catheter body 12 to the interior space of the balloon 52. Inflation and deflation of balloon 52 are accomplished by applying and withdrawing pressurized fluid to and from the lumen 20 through the valve adaptor 40 in a manner well known in the art.

The delivery lumen 22 is coupled by through hole 23 to the lumen 57 of delivery tube extension 56. The delivery tube extension 56 is formed of a flexible, thin walled tube cemented alongside the balloon 52 externally to the balloon wall for the full length of the balloon 52 between the proximal and distal junctions 54 and 55. The through hole 23 extends through the side wall of delivery tube extension 56, which is cemented proximally to itself and the surface of the catheter body distal end segment 14, and makes a communication between the delivery tube extension lumen 57 and delivery lumen 22. The delivery tube extension lumen 57 is stopped up or filled, or adhered to itself, at its distal end lumen 62 distal to the delivery exit port 60 formed in its external facing wall.

The guide wire lumen 18 is open through the soft tip 34, which is preferably tapered in a manner well known in the balloon catheter art, and distal aperture 36. Several of the balloon inflation/deflation holes 58 through the inflation/deflation lumen 20 are depicted. The balloon 52 is preferably formed of a radiation cross-linked polyolefin, e.g. polyethylene, which does not readily adhere to the occluding agent contacting it during delivery and formation of the occluding castand attached to the exterior surface of the catheter body 12 by adhesive bonding or thermal bonding or welding at the proximal and distal junctions 54 and 55 in a manner well known in the art of fabricating miniature balloon catheters. The delivery extension tube may be formed of a thin walled TEFLON or polyethylene tube and adhered to the balloon 52 by adhesive bonding or thermal welding or bonding. The balloon and delivery extension tube may also be coated with a release agent when fabricated of certain materials more prone to stick to the particular delivery agent.

Referring now to FIG. 4B, it depicts, in an end cross section view conforming generally to FIG. 4A, the above described features of the construction of the distal end segment 16 and balloon 52 in accordance with a fabrication variation that may be employed in the first embodiment and is also depicted in FIG. 7. In this variation, the delivery exit port 60 is formed in the outer wall of the balloon 52, and the delivery tube extension 56 is formed during balloon wall extrusion of the tubular shaped balloon. The exit port 60 is formed in the delivery tube extension 56 communicating with the lumen therein extending along the balloon 52 back to the proximal junction 54 and the through hole 23, as also shown in cross section in conjunction with the further embodiment of FIG. 7.

The orientation of the delivery exit port 60 to the blood vessel opening is preferably determined through the use of the radiopaque markers 15 and 17 around the port 60 which may be observed during introduction and position through fluoroscopy. The proper seal afforded by the inflated balloon may be verified in the further steps of inflating the balloon 52, injecting a contrast medium through the delivery lumen 22 and exit port 60 after orienting the delivery exit port 60 to a trial position and observing the filling of the aneurysm as well as the absence of its leakage down the blood vessel lumen when it is properly oriented. Alternatively, a radiopaque tip probe may be introduced down the delivery lumen 22 and observed as it exits the exit port 60 and enters the aneurysm chamber or a pressure measurement may be taken.

In the embodiments described above, a liquid occluding agent is preferably introduced into the chamber of the aneurysm where it reacts with blood or tissue or solidifies to fill the space. Such occluding agents may include cross-linked collagen implant fibrils which may be mixed with contrast media and chemical buffers of the types described in the '718 patent. A liquid or paste collagen is available under the name HELIOSTAT. A further liquid thrombin mixture in available under the name THROMBOSTAT. Such thrombin and collagen including mixtures form an occluding cast by thrombus formation.

Other liquid, single component, occluding agents include methyl cyanoacrylate adhesives or 2-hydroxyethyl methylacrylate (HEMA) which set on contact with body fluids, e.g. of the type described in U.S. Pat. No. 4,207,891 directed to occluding Fallopian tubes. In addition, liquid silicone rubber may be used.

Solid, single component, occluding agents may also be used in solid fibrous or particulate form that may be delivered through the vessel opening to form a solid mask of thrombus. The occluding agent is effective to coagulate blood around the fibers or particles and to form the thrombus mass within the aneurysm chamber or peripheral vessel to function as a solid occluding cast. Such occluding agents may also include one of the group of particulate compounds comprising polyvinyl alcohol (PVA), IVALON, and GELL FOAM which are reactive to blood to coagulate it on contact, as described by Purdy in "Pre-Operative Embolization of Cerebral Artereovenous Malformations with Polyvinyl Alcohol Particles", AJNR 11:501–510, May/June, 1990.

It will also be appreciated that a solid occluding device or devices may be introduced through the lumen 22, out the delivery exit port 60 and through the adjoining vessel opening. For example, the wire coils described in the above referenced '437 patent may be so introduced, while the balloon 52 is inflated, to fill the aneurysm chamber or branch vessel from the vessel opening. Once introduced, a plurality of such coils entwine or catch on one another and the aneurysm or vessel side walls to provide acute fixation end encourage the formation of a mass of thrombus that forms the occluding cast.

A further feature of the invention is depicted in FIGS. 3 and 4A–4B which allows the use of the balloon catheter 10 with certain occluding agents that are liquid until they are exposed to irradiating illumination of a frequency which causes the occluding agent to solidify. In this respect, a miniature probe or optical fiber 66 having a light diffuser or lens 68 at its distal end may be introduced down the lumen 22 (or lumen 20) and positioned to radiate light of the required frequency toward the opening 60. The catheter body 12 and balloon 52 may be transmissive of the frequency of radiation emitted, so that it falls upon occluding agent after it is delivered through the delivery exit port 60. Optionally, the balloon catheter 10 may be rotated within the vessel after the occluding agent is delivered to seal the aneurysm or branch vessel opening with the inflated balloon 52. The optical fiber 66 and diffuser 68 may be oriented to emit radiation through the catheter body distal end segment 16 and balloon 52 and toward the blood vessel opening to effect the curing of the occluding agent and the formation of the occluding cast. In FIGS. 4A and 4B, the optical fiber 66 and diffuser 68 are depicted preferably extending down the inflation/deflation lumen 20 and optionally down the delivery lumen 22, respectively. The optical fiber 66 and probe 68 may be extended down the inflation/deflation lumen 18 or the aspirating/venting lumens of the other embodiments as well.

In this variation, the occluding agent preferably compromise one of the group of light reactive compounds including urethane oligomer/(meth) acrylate monomer blends reactive to light in the ultraviolet range and particularly the compound Dymax 136-M which is reactive to ultraviolet light of a frequency of 300–400 nanometers. Such compounds and light sources for their curing are described In the Dymax MD selector guide, Dymax data sheets and the Dymax 10M catalog.

As mentioned above, the lumens 18, 20 and 22 may be selectively configured to accommodate a two component occluding agent in a further embodiment of the invention depicted in partial cross section, elongated views of the distal end segment 16 in FIGS. 5 and 7, and in their respective end cross-section views in FIGS. 6 and 8. In order to use both of the lumens 20 and 22 as delivery lumens, it is preferable to provide a further delivery exit port 60' and delivery tube lumen 61' extending from lumen 20 and through its wall in the catheter body distal end segment 16 closely adjacent to the delivery exit port 60 coupled to the delivery lumen 20.

Furthermore, it is preferable to employ the guide wire lumen 18 as the inflation/deflation lumen and to provide inflation/deflation holes 58 through its wall into the interior space of the balloon 52. And, in order to allow the guide wire to be extended through the elongated, tapered soft tip 34 and distal aperture 36, a self sealing valve 46 which is penetrable by the guide wire 70 is formed adjacent to the distal aperture 36. Such a self sealing valve 46 provides sufficient sealing against inflation pressure to allow inflation of the balloons 52 when the guide wire 70 is or is not extending through the valve 46 and may be of the type described in U.S. Pat. No. 5,005,635 to Cragg, incorporated herein by reference.

In the embodiment of FIGS. 3 and 6, the lumen 20 is coupled to the lumen 61' of a further delivery tube extension 56' extending to the additional delivery exit port 60'. The further delivery tube extension 56' may be formed internal to the balloon or external to the balloon as a separate tube, as described above.

The balloon 52 depicted in FIGS. 6 and the preceding figures is generally cylindrical, encircling and extending along the catheter body distal end segment 16, so that the delivery exit port(s) are laterally displaced with the expanding balloon during inflation. In a further embodiment of the invention, the delivery exit port(s) 60, 60' are formed through the catheter body distal end segment 16, and an alternate balloon structure 52' is attached around only a major circumferential arc of the segment 16. The alternate balloon 52' configurations are depicted in a partial cross section, elongated view and end views of the distal end segment 16 in FIGS. 7, 8A, 8B and 8C.

In this embodiment and its depicted variations, alternate balloon 52' is formed along only a major circumferential section of the distal end segment 16 (FIGS. 8A and 8B) or a minor circumferential interior section of the tubular balloon in adhered along the outer surface of tube 13 (FIG. 8C) so that the balloon 52' only inflates around the major circumference of the distal end segment 16. The delivery exit ports 60, 60' (or port 60) are formed through the outer tube 13 of the segment 16 in the minor circumferential section thereof in direct communication with the lumens 22 and 20 formed therein. The delivery exit ports 60 and 60', as shown in FIGS. 7 and 8C are thus directly made to the lumens 22 and 20, respectively, through the adhered balloon wall 52' and outer tube 13. The balloon 52' is inflated and deflated through the openings 58 made in the side wall of the catheter body distal end segment 16 to the lumen 18, which also functions as the guide wire lumen.

As also depicted in FIGS. 8A–8C, the alternate balloon 52' can be formed to have alternate shapes when inflated. Each of the balloons 52' are as roughly semi-circular and surrounding a major arc of the circumference of the distal end segment 16. The delivery exit ports 60 and 60' are formed in a minor circumferential arc or section of the distal end segment 16 of the catheter body 12. In FIG. 8B, the balloon 52' forms a U-shaped perfusion channel 53, when inflated, along its length opposite to the minor section where the exit ports 60 and 60' are located. This alternate shape depicted in FIG. 8B allows the balloon 52' to form the perfusion channel 53 with the blood vessel wall through which blood may continue to flow after the balloon is inflated in the vessel. In the other balloon shapes described above, it may be desireable to employ a separate perfusion catheter bypassing the balloon catheter 10 to provide perfusion while the occluding cast forms.

In the two component embodiment and these alternate configurations, the first and second components of an occluding agent may be delivered through the lumens 20 and 22 to exit the ports 60 and 60' after the balloon is inflated to position the ports against the opening of the aneurysm chamber. Such delivery is depicted in FIG. 8A. The components mix together inside the aneurysm chamber or lumen of the branch vessel, and the resulting reaction solidifies the components to form the occluding cast therein. One example of a two component occluding agent would be catalyzable polyester monomers or epoxies.

FIG. 8B also depicts the alternative use of the balloon catheter to deliver a single component occluding agent of the various types described above along with aspiration and/or ventilation of the contents of the aneurysm chamber or branch vessel lumen. In FIG. 8B, the lumen 20 and delivery exit port 60' may be coupled at the proximal end 26 connectors to an aspirator to initially aspirate the contents of a branch blood vessel or aneurysm after the blood vessel opening is sealed. In addition or alternatively, the lumen 20 may be coupled to operate as a venting lumen to allow the contents to flow out as the occluding agent is delivered into the blood vessel opening through the delivery lumen 22 and exit port 60.

The above described features of the balloon catheter 10 of this embodiment with the alternate balloon 52' may be employed with only a single delivery lumen 22 and exit port 60, in the fashion of FIGS. 3 and 4 described above, to deliver a single component occluding agent. In this regard, FIG. 7 may represent such a cross section of only a single delivery lumen 22 and exit port 60.

All of the above described embodiments and variations thereof may be implemented in the co-axial tube, preferably integral balloon configuration for the catheter body 12, including the catheter body proximal and distal end segments 14 and 16, as depicted in FIGS. 9–11. In the co-axial tube embodiment, the inner tube 11 is surrounded by an outer tube 13 to form the interior guide wire lumen 18 and the inflation lumen 20. The outer tube 13 can be fabricated to form the inflation balloon 52 integrally with it in the fashion disclosed in the Simpson-Roberts U.S. Pat. No. 4,323,071 in a manner well known in the balloon catheter art.

The single delivery lumen 22 is formed as shown in FIGS. 10A and 11A in the outer tube 13 extending the full length of the catheter body 12 and in the outer wall of the balloon 52 by standard multi-lumen extrusion techniques. The single delivery exit port 60 is formed as depicted in FIG. 10A in the outer membrane of the outer tube 13 by standard skiving or porting techniques also well known in the balloon catheter fabrication art.

FIGS. 10B and 11B depict the addition of the second delivery or venting lumen 22' leading to the second delivery exit or venting port 60' for the applications described above. Thus, in this embodiment, the catheter body 12 is provided with four lumens. The configuration and construction of the embodiments of FIGS. 9–11 allows the catheter body 12 and balloon 52 to be integrally formed simply and with a low profile with a plurality of lumens formed in the outer tube 13 and balloon 52. Moreover, by adhering the balloon interior surface to the inner tube 11, in the manner of the embodiment of FIG. 8C, the shapes of balloon 52' of FIGS. 7 and 8 may be employed with the features of this embodiment.

Turning now to the methods of use of the embodiments described above, reference is made to FIGS. 12 through 16 which are illustrations of an aneurysm 80 in an artery 90 and the steps of introducing and positioning a deflated balloon catheter, inflating the catheter, delivering the occluding agent, forming the cast and withdrawing the balloon catheter. Aneurysm 80 is formed through vessel opening 82 as a thin walled chamber 84 defined by wall 86. FIG. 17 is a single illustration of the inflation and delivery of the occluding agent into the opening of a branch vessel corresponding to FIG. 14B to illustrate that the same steps of FIGS. 12–16 would be employed in that method.

The introduction of the balloon catheter 10 through the arterial or venous system may be preceded by the introduction of the guide wire 70 in any of the various approaches employed in PTCA or balloon angioplasty. Once the guide wire is positioned, the balloon catheter 10, with the balloon 52 deflated, may be introduced over the guide wire 70 as depicted in FIG. 12A. Alternatively, the guide wire 70 may be permanently attached to or positioned in the guide wire lumen 18 extending out the distal tip aperture 36 and/or valve 46, and the assembly may be advanced through the blood vessels until the deflated balloon 52, 52' is positioned and inflated as depicted in FIG. 13A. The end views of FIGS. 12B and 13B depict these steps of positioning the guide wire 70 through the main vessel lumen 94 alongside the vessel or aneurysm opening 82 and inflating the balloon 52, 52'.

A guide catheter and/or introducer shrouding the balloon catheter 10 may also be employed in the introduction procedure, as is well known in the art. The progress of introduction is typically observed under fluoroscopy and sided by the earlier identification of the aneurysm or branch vessel by radiopaque media which persists during the introduction and positioning steps.

FIG. 12A is thus a schematic side view illustration of the aneurysm in an artery and the positioning of a deflated balloon catheter distal end segment 16 in relation to the aneurysm opening in accordance with the invention. It will be understood that a separate venting catheter 88 may also be positioned alongside the balloon catheter 10 so that the contents of the aneurysm chamber 84 may be aspirated and/or vented out as occluding agent is delivered through the delivery exit port 60, if the balloon catheter 10 is not configured to provide internal aspirating/venting as described above. Moreover, it will be understood that the balloon catheter of the invention in its various embodiments may be employed with a perfusion catheter 96 of any known type placed alongside the balloon 52, or in the U-shaped perfusion channel of the balloon 52', opposite to the opening 82. The perfusion catheter 96 allows blood flow past the temporary obstruction of the blood vessel 90 during the procedure without affecting the seal of the balloon to the vessel wall 92 afforded by the inflated balloon.

In this regard, once the balloon 52, 52' is positioned, it is oriented by twisting the proximal catheter body segment 14 so that the delivery exit port(s) 60, 60' is oriented facing the opening 82. The balloon positioning and orientation is observed under fluoroscopy to align the radiopaque markers 15, 17 to the opening 82. Testing of the seal may be accomplished by a test inflation while contrast medium is delivered as described above and as shown in FIGS. 14A and 14B. The test inflation may be avoided if the occluding agent is mixed with contrast media as described above. Alternatively, pressure readings may be taken through the delivery lumen to determine the adequacy of the balloon seal.

After the orientation and inflation is deemed acceptable, the delivery of the occluding agent or device may be accomplished. As the occluding agent is delivered, it either reacts with or displaces the fluid and blood clots in the chamber 84 and makes contact with the chamber wall 86. The delivery is depicted in FIGS. 14A and 14B.

The fully delivered occluding agent forming an occluding cast is illustrated in FIGS. 15A and 15B. As described above, the delivered occluding agent may be solidified through a number of alternative operations to form the occluding cast 100. During such occlusion, blood flow through the perfusion catheter or channel 53 afforded by the balloon shape may be continued.

After occlusion is completed and the occluding cast 100 is formed, the balloon 52 may be deflated and withdrawn along the guide wire 70. The guide wire 70 may then be removed.

Optionally, the balloon catheter 10 may be rotated after the delivery step of FIGS. 14A and 14B to re-orient the delivery exit opening(s) 60, 60' away from the opening 82 and seal the vessel opening 82 with the exterior side wall of the inflated balloon 52.

In this regard, it is necessary that the balloon catheter 10 be torsionally rigid enough down the length of the catheter body 12 to transmit rotational torque applied manually at its proximal end segment 14 to its distal end segment 16 in order to rotate the inflated balloon. Increased torque transmission ability may also be useful in introducing the catheter 10 and orienting the delivery exit port(s) 60, 60' to the vessel opening 82. It may therefore be desireable to increase the torque by providing a coupling of the distal segment of guide wire 70 with the lumen 18 or exit port 36 to allow torque to be transmitted by the guide wire. Alternatively, the guide wire may be fixedly attached permanently in the catheter lumen 18.

FIG. 18 depicts an alternate distal end segment of the balloon catheter of the embodiment of FIG. 7 having a permanently installed torque wire 71 attached distally therein by adhesive 72 to the soft tip 34 for increasing the torque transfer for allowing rotation of the balloon. The distally attached twist wire 71 is otherwise free in lumen 18 and may be coupled proximally to a knob to allow it to be twisted by the physician in the manner well known in the art and disclosed in U.S. Pat. No. 4,582,181. It will be understood that this feature may be implemented in all of the embodiments described above by substitution with the guide wire 70 and associated structure.

The above described method is applicable as well to the occlusion of branch vessels 102 through a branch vessel opening 104 into the main vessel 90. FIG. 17 depicts the intermediate step of that process, that is delivering the occluding agent into the branch vessel 102 through the opening 104, corresponding to FIG. 14A. Each of the preceding and subsequent steps illustrated in FIGS. 12–16 may be followed in practicing the invention for the occlusion of branch vessels involving any of the preferred embodiments of the invention.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

PARTS LIST aneurysm occluding balloon catheter 10
inner tube 11
catheter body 12
outer tube 13
catheter body proximal end segment 14
first radiopaque marker 15
catheter body distal end segment 16
second radiopaque marker 17
guide wire lumen 18
webs 19 and 21
inflation/deflation lumen 20
delivery lumen 22
additional delivery or venting lumen 22'
through hole 23
aperture 24
catheter proximal end connector assembly 26
fitting 28
single lumen tube 30
manifold 32
soft tip 34
distal aperture 36
adaptor fitting 38
valve adaptor 40
tube 42
self sealing, penetrable, distal tip valve 46
valve adaptor 48
tube 50
balloon 52
alternate configuration balloon 52'
U-shaped perfusion channel 53
proximal junction 54
distal junction 55
elastic delivery tube extension 56
additional elastic delivery tube extension 56'
delivery tube extension lumen 57
inflation/deflation holes 58
delivery exit port 60
additional delivery exit or venting port 60'
delivery tube lumen 61
additional delivery tube or venting tube lumen 61'
filled distal most extension tube lumen 62
filled distal most delivery lumen 63
filled distal most inflation/deflation lumen 64 1
optical fiber 66
light radiation diffuser 68
guise wire 70
twist wire 71
adhesive 72
aneurysm 80
aneurysm opening 82
aneurysm chamber 84
aneurysm wall 86
venting catheter 88S
main vessel 90
main vessel wall 92
main vessel lumen 94
bypass catheter 96
occluding cast 100
branch vessel 102
branch vessel opening 104

What is claimed is:

1. A method of forming an occluding cast through a vessel opening in the side wall of a main blood vessel for occluding a peripheral vessel or aneurysm outside of the opening without occluding the main vessel, comprising the steps of:

sealing the main vessel lumen and side walls from the vessel opening into the aneurysm or peripheral vessel to thereby shield the main vessel wall adjacent to the vessel openings;

delivering an occluding agent through the vessel opening into the aneurysm chamber or peripheral vessel; and maintaining the seal until occlusion is effected or the occluding agent is stabilized, whereby an occluding cast is formed by or about the occluding agent within the aneurysm or peripheral vessel and seals the vessel opening without occluding the main vessel.

2. The method of claim 1 further comprising the step of:
perfusing the vessel lumen to allow blood flow through it in perfusion channel sealed from the vessel opening during delivery of the occluding agent and maintenance of the seal.

3. The method of claim 1 further comprising the step of:
venting through the vessel opening leading to the aneurysm chamber or peripheral vessel during delivery of the occluding agent.

4. The method of claim 1 further comprising the step of:
aspirating the contents of the aneurysm chamber or peripheral vessel prior to delivery of the occluding agent.

5. The method of claim 1 wherein said sealing and delivering steps further comprise the steps of:
introducing a balloon catheter having an inflatable balloon into a position in the main vessel adjacent to the vessel opening;
introducing means for delivering an occluding agent through a delivery exit port into a position in the main vessel adjacent to the vessel opening to deliver the occluding agent through the vessel opening;
inflating the balloon to fill the blood vessel and to seal the delivery exit port and the vessel opening from the blood vessel lumen; and
delivering the occluding agent through the delivery lumen and delivery exit port and through the vessel opening.

6. The method of claim 5 further comprising the step of:
rotating the balloon catheter to rotate the inflated balloon across the vessel opening after delivering the occluding agent, whereby the vessel opening is sealed from the main vessel lumen as the occluding agent forms the occluding cast.

7. The method of claim 1 wherein the delivering step further comprises:
delivering an occluding agent having a liquid form through the vessel opening, the occluding agent being reactive to irradiating light for solidifying as a solid occluding cast; and
further comprising the step of:
irradiating the occluding agent delivered through the vessel opening with irradiating light directed through the vessel opening sufficiently to effect solidification of the delivered liquid occluding agent.

8. The method of claim 1 wherein the delivering step further comprises:
delivering an occluding agent having a solid fibrous or particulate form through the vessel opening to form a solid mass of thrombus, the occluding agent effective to coagulate blood around the fibers or particles and to form a solid thrombus mass within the aneurysm chamber or peripheral vessel functional as a solid occluding cast.

9. The method of claim 1 wherein the delivering step further comprises:
delivering an occluding agent comprising one or more compressible shaped members having an expanded form when unconfined and compressible for delivery through a confined space and through the vessel opening, and specifically a coil or coils of noble metals.

10. The method of claim 1 wherein the delivering step further comprises:

delivering an occluding agent having a liquid form through the vessel opening, the occluding agent being reactive on exposure to form the solid occluding cast.

11. The method of claim 1 wherein said sealing and delivering steps further comprise the steps of:
introducing a balloon catheter having an inflatable balloon and a delivery lumen extending therethrough terminating in a delivery exit port into a position in the main vessel adjacent to the opening;
orienting the delivery exit port to the opening;
inflating the balloon to fill the blood vessel and to seal the delivery exit port and the opening from the blood vessel lumen; and
delivering the occluding agent through the delivery lumen and delivery exit port and into the opening.

12. The method of claim 1 wherein said sealing and delivery steps further comprise the stops of:
introducing a balloon catheter having an inflatable balloon and a delivery lumen and a further lumen extending therethrough terminating in a delivery exit port and a further exit port into a position in the main vessel adjacent to the vessel opening;
orienting the exit ports to the vessel opening;
inflating the balloon to fill the blood vessel and to seal the exit ports and the vessel opening from the blood vessel lumen;
delivering the occluding agent through the delivery lumen and delivery exit port and through the vessel opening; and
venting the contents of the aneurysm chamber or peripheral vessel through the vessel opening and through the further exit port and further lumen during delivery of the occluding agent through the delivery lumen and delivery exit port and through the vessel opening, whereby the occluding agent displaces the contents of the peripheral vessel or aneurysm distal to the vessel opening to form the occluding cast therein.

13. The method of claim 12 further comprising the step of:
aspirating the contents of the aneurysm chamber or branch vessel through one of the delivery or further lumens and the vessel opening before delivering the occluding agent.

14. The method of claim 1 wherein said sealing and delivery steps further comprise the steps of:
introducing a balloon catheter having an inflatable balloon and first and second delivery lumens extending therethrough terminating in first and second delivery exit ports into a position in the main vessel adjacent to the vessel opening;
orienting the delivery exit ports to the vessel opening;
inflating the balloon to fill the blood vessel and to seal the delivery exit ports and the vessel opening from the blood vessel lumen;
delivering a first component of the occluding agent through the first delivery lumen and first delivery exit port and into the opening; and
delivering a second component of the occluding agent through the second delivery lumen and second delivery exit port and into the opening, whereby the first and second components of the occluding agent mix together in the peripheral vessel or aneurysm distal to the vessel opening to form the occluding cast therein.

15. The method of claim 14 further comprising the step of:
aspirating the contents of the aneurysm chamber or branch vessel through one of the first or second delivery lumens and the vessel opening before delivering the first and second components of the occluding agent.

16. Apparatus for forming an occluding cast through a vessel opening in the side wall of a main blood vessel for occluding a peripheral vessel or aneurysm chamber outside of the vessel opening without occluding the vessel lumen comprising:

means positionable within the main vessel lumen for temporarily sealing the main vessel side wall and vessel lumen from the vessel opening into the aneurysm or peripheral vessel to thereby shield the main vessel wall adjacent to the vessel opening;

means for delivering an occluding agent through the vessel opening leading to the aneurysm chamber or peripheral vessel; and means for maintaining the sealing of the main vessel wall and vessel lumen until occlusion is effected or the occluding agent is stabilized, whereby an occluding cast is formed by or about the occluding agent within the aneurysm chamber or peripheral vessel and seals the vessel opening without occluding the main vessel.

17. The apparatus of claim 16 further comprising:

means for aspirating through the vessel opening leading to the aneurysm chamber or peripheral vessel before delivering the occluding agent.

18. The apparatus of claim 16 further comprising:

means for perfusing the vessel lumen to allow blood flow through it in perfusion channel sealed from the vessel opening during delivery of the occluding agent and maintenance of the seal.

19. The apparatus of claim 16 further comprising:

means for venting through the vessel opening leading to the aneurysm chamber or peripheral vessel during delivery of the occluding agent.

20. The apparatus of claim 16 wherein the occluding agent has a liquid form for delivery through the vessel opening, the occluding agent being reactive to irradiating light for solidifying as a solid occluding cast, and further comprising:

means for irradiating the occluding agent delivered through the vessel opening with light directed through the vessel opening sufficiently to effect solidification of the delivered liquid occluding agent.

21. The apparatus of claim 16 wherein the occluding agent has a liquid form for delivery through the vessel opening, the occluding agent being reactive on exposure to form the solid occluding cast.

22. The apparatus of claim 16 wherein the occluding agent has a solid particulate form for delivery through the vessel opening, the occluding agent effective to coagulate blood around the particles and to form a solid thrombus mass within the aneurysm chamber or peripheral vessel functional as a solid occluding cast.

23. The apparatus of claim 16 wherein the occluding agent further comprises a compressible shaped member having an expanded form when unconfined and compressible for delivery through a confined space and through the vessel opening, and specifically a coil or coils of noble metals.

24. The apparatus of claim 16 wherein said sealing means further comprises:

an elongated balloon catheter having an inflatable balloon;

means for introducing the balloon catheter into a position in the main vessel adjacent to the vessel opening; and means for inflating the balloon to fill the blood vessel lumen and to seal the delivery exit port and the vessel opening from the blood vessel lumen; and wherein said delivering means further comprises:

means for positioning a delivery exit port in position in the main vessel adjacent to the vessel opening to deliver the occluding agent through the vessel opening; and means for delivering the occluding agent through said delivery exit port and through said vessel opening.

25. The apparatus of claim 24 further comprising:

means for rotating the balloon catheter to rotate the inflated balloon across the vessel opening after delivering the occluding agent, whereby the vessel opening is sealed from the main vessel lumen as the occluding agent forms the occluding cast.

26. The apparatus of claim 24 further comprising:

means for perfusing the vessel lumen to allow blood flow through it in perfusion channel sealed from the vessel opening during delivery of the occluding agent and maintenance of the seal by said inflated balloon.

27. The apparatus of claim 16 wherein said sealing and delivery means further comprise:

a balloon catheter having an inflatable balloon and a delivery lumen and a further lumen extending therethrough terminating in a delivery exit port and a further exit port;

means for introducing the balloon catheter into a position in the main vessel lumen adjacent to the vessel opening and for orienting the delivery and further exit ports to the vessel opening;

means for inflating the balloon to fill the blood vessel and to seal the exit ports and the vessel opening from the blood vessel lumen;

means for delivering the occluding agent through the delivery lumen and delivery exit port and through the vessel opening; and means for venting the contents of the aneurysm chamber or peripheral vessel through the vessel opening and through the further exit port and further lumen during delivery of the occluding agent through the delivery lumen and delivery exit port and through the vessel opening, whereby the occluding agent displaces the contents of the peripheral vessel or aneurysm chamber distal to the vessel opening to form the occluding cast therein.

28. The apparatus of claim 27 further comprising:

means for aspirating the contents of the aneurysm chamber or branch vessel through one of the delivery or further lumens and the vessel opening before delivering the occluding agent.

29. The apparatus of claim 16 wherein:

said sealing means further comprise:

a balloon catheter having an inflatable balloon and first and second delivery lumens extending therethrough terminating in first and second delivery exit ports;

means for introducing the balloon catheter into a position in the main vessel adjacent to the vessel opening and orienting the delivery exit ports to the vessel opening; and means for inflating the balloon to fill the blood vessel and to seal the delivery exit ports and the vessel opening from the blood vessel lumen; and said delivery means further comprise:

means for delivering a first component of the occluding agent through the first delivery lumen and first delivery exit port and into the vessel opening; and means for delivering a second component of the occluding agent through the second delivery lumen and second delivery exit port and into the vessel opening, whereby the first and second components of the occluding agent mix together in the peripheral vessel or aneurysm chamber distal to the vessel opening to form the occluding cast therein.

30. The apparatus of claim 29 further comprising:

means for aspirating the contents of the aneurysm chamber or branch vessel through one of the first or second delivery lumens and the vessel opening before delivering the first and second components of the occluding agent.

31. A balloon catheter for delivering an occluding agent in situ into a vessel opening in the side wall of a main blood vessel and for forming an occluding cast in situ for occluding a peripheral, branch blood vessel or aneurysm chamber distal to the vessel opening without occluding the main blood vessel lumen comprising:

an elongated catheter body having a proximal end segment and a distal end segment adapted to be introduced into the main blood vessel lumen in relation to the vessel opening leading to the branch blood vessel or aneurysm chamber;

an inflatable balloon attached at the distal end segment of said catheter body into which inflation fluid may be delivered to inflate the balloon and withdrawn to deflate the balloon;

delivery means having a delivery lumen extending from the proximal to the distal end segment of the catheter body and having an exit port in communication therewith for delivering an occluding agent to the vessel opening when positioned with respect thereto; and inflation means for inflating the balloon with inflation fluid to effect the inflation thereof within the main blood vessel lumen to form a seal of the main blood vessel around and on either side of the vessel opening and to position said delivery exit port in alignment with the vessel opening, whereby the occluding agent may be delivered through the vessel opening.

32. The balloon catheter of claim 31 wherein said inflation means further comprises:

an inflation lumen extending from the proximal segment to the distal segment of said catheter body and adapted to be coupled at the proximal segment to a source of inflation fluid and at the distal segment to said interior inflation space; and said delivery means delivery lumen extends from the proximal segment to the distal segment of said catheter body and is adapted to be coupled at the proximal segment to a source of an occluding agent and at the distal segment to said delivery exit port situated alongside said balloon.

33. The balloon catheter of claim 32 wherein:

said balloon is formed of a balloon wall extending along said distal end segment of said catheter body and around the circumference thereof, whereby said balloon is inflatable outwardly from said distal end segment against the wall of a blood vessel on operation of said inflation means; and said delivery lumen is formed on and extends along said balloon wall a predetermined distance and is formed with said delivery exit port which faces away from said balloon and said distal end segment, whereby inflation of said balloon laterally extends said delivery exit port against a vessel opening in the wall of a blood vessel.

34. The balloon catheter of claim 33 further comprising:

a further lumen extending from the proximal segment to the distal segment of said catheter body and formed on and extending along said balloon wall a predetermined distance to a further exit port which faces away from said balloon and said distal end segment, whereby inflation of said balloon laterally extends said further exit port against said vessel opening;

means at the proximal end segment of said catheter body selectively adapted to couple said further lumen to deliver a component of a two component occluding agent through said further exit port and through said vessel opening, to aspirate the contents of the aneurysm chamber or branch vessel through one of the delivery or further lumens and the vessel opening before delivering the occluding agent, and to vent the contents of the aneurysm chamber or peripheral vessel through the further vessel opening and through the further exit port and further lumen during delivery of the occluding agent through the delivery lumen and delivery exit port and through the vessel opening, whereby the occluding agent displaces the contents of the peripheral vessel or aneurysm distal to the vessel opening to form the occluding cast therein.

35. The balloon catheter of claim 32 wherein:

said balloon is formed of a balloon wall extending along said distal end segment of said catheter body and around at least a major section of the circumference thereof, whereby said balloon is inflatable outwardly from said distal end segment against the wall of a blood vessel on operation of said inflation means to fill the blood vessel lumen and displace the minor section of the circumference of said distal end segment of said catheter body against the blood vessel wall; and said delivery exit port is formed in said minor section of the circumference of said distal end segment a predetermined distance along the length of said balloon and faces away from said balloon, whereby inflation of said balloon laterally extends said delivery exit port against a vessel opening in the wall of a blood vessel.

36. The balloon catheter of claim 35 further comprising:

a further lumen extending from the proximal segment to the distal segment of said catheter body to a further exit port, said further exit port formed in said minor section of the circumference of said distal end segment a predetermined distance along the length of said balloon facing away from said balloon, whereby inflation of said balloon laterally extends said delivery exit port against the vessel opening in the wall of a blood vessel; and means at the proximal end segment of said catheter body selectively adapted to couple said further lumen to deliver a component of a two component occluding agent through said further exit port and through said vessel opening, to aspirate the contents of the aneurysm chamber or branch vessel through one of the delivery or further lumens and the vessel opening before delivering the occluding agent, and to vent the contents of the aneurysm chamber or peripheral vessel through the further vessel opening and through the further exit port and further lumen during delivery of the occluding agent through the delivery lumen and delivery exit port and through the vessel opening, whereby the occluding agent displaces the contents of the peripheral vessel or aneurysm distal to the vessel opening to form the occluding cast therein.

37. The balloon catheter of claim 35 further comprising:

means for forming a perfusion, channel between said balloon wall extending along said distal end segment of said catheter body and the main blood vessel wall sealed from said vessel opening upon inflation of said balloon.

38. The balloon catheter of claim 35 wherein:

said balloon is formed of a tubular balloon wall adhered to said catheter body along said distal end segment of said catheter body in said minor section of the circumference thereof to form an adhered balloon section, whereby said balloon is inflatable outwardly from said distal end segment against the wall of a blood vessel on operation of said inflation means to fill the blood vessel lumen and displace the minor section of the circumference of said distal end segment of said catheter body and said adhered balloon section against the blood vessel wall; and said delivery exit port is formed in said minor section of the circumference of said distal end segment a predetermined distance along the length of and through said adhered balloon section and faces away from said balloon, whereby inflation of said balloon laterally extends said delivery exit port against a vessel opening in the wall of a blood vessel.

39. The balloon catheter of claim 31 further comprising:

means for forming a perfusion channel between said balloon wall extending along said distal end segment of said catheter body and the main blood vessel wall sealed from said vessel opening upon inflation of said balloon.

40. The balloon catheter of claim 31 wherein:

said distal segment end of said catheter body includes a distal extension terminating in a tip extending distally to said balloon; and said inflation means further comprises an inflation lumen extending from the proximal segment to the distal tip of said catheter body through said inflation lumen adapted to be coupled at the proximal segment end to a source of inflation fluid and at the distal segment end to said interior inflation space of said balloon; and further comprising:

a guide wire for providing guidance of said distal end segment into position with respect to a vessel opening;

means at said proximal end segment of said catheter body for receiving said guide wire in said inflation lumen; and valve means formed in said distal tip and across said inflation lumen for sealing said inflation lumen from the loss of inflation fluid during inflation of said balloon and for receiving said guide wire extending distally therethrough during introduction and positioning of said balloon catheter.

41. The balloon catheter of claim 31 wherein:

said distal segment end of said catheter body includes a distal extension terminating in a tip extending distally to said balloon; and said inflation means further comprises an inflation lumen extending from the proximal segment to the distal tip of said catheter body through said inflation lumen adapted to be coupled at the proximal segment end to a source of inflation fluid and at the distal segment end to said interior inflation space of said balloon; and further comprising:

a twist wire for providing guidance of said distal end segment into position with respect to a vessel opening and for providing torque transfer from the proximal segment of said catheter body to said distal tip to provide rotational movement thereof;

means at said proximal end segment of said catheter body for receiving said twist wire in said inflation lumen; and means formed in said distal tip and across said inflation lumen for sealing said inflation lumen from the loss of inflation fluid during inflation of said balloon and for receiving and attaching said twist wire extending distally therethrough during introduction and positioning of said balloon catheter.

42. The apparatus of claim 31 wherein the occluding agent has a liquid form for delivery through the vessel opening, the occluding agent being reactive to irradiating light for solidifying as a solid occluding cost, and said apparatus further comprises:

a source of irradiating light;

means for directing said irradiating light into the occluding agent delivered through the vessel opening sufficiently to effect solidification of the delivered liquid occluding agent.

43. The apparatus of claim 31 wherein:

said catheter body further comprises an inner elongated tube and an outer elongated tube in co-axial alignment to form an inner lumen and an outer lumen; and said balloon is formed of said outer tube in said distal end segment thereof; and wherein:

said inflation means comprises said outer lumen; and said delivery lumen is formed within said outer tube and extends form said proximal to said distal segment terminating in said delivery exit port.

* * * * *